United States Patent
Sun et al.

(10) Patent No.: US 9,636,352 B2
(45) Date of Patent: May 2, 2017

(54) COMPOSITIONS AND METHODS FOR THE TREATMENT OF MUSCULOSKELETAL RELATED DISEASES AND DISORDERS USING METAL ION-CITRATE ANALOG COMPLEXES

(75) Inventors: Yubo Sun, Charlotte, NC (US); Edward N. Hanley, Charlotte, NC (US)

(73) Assignee: THE CHARLOTTE-MECKLENBURG HOSPITAL AUTHORITY, Charlotte, NC (US)

(*) Notice: Subject to any disclaimer, the term of this patent is extended or adjusted under 35 U.S.C. 154(b) by 169 days.

(21) Appl. No.: 13/418,125

(22) Filed: Mar. 12, 2012

(65) Prior Publication Data

US 2012/0238521 A1 Sep. 20, 2012

Related U.S. Application Data

(60) Provisional application No. 61/453,401, filed on Mar. 16, 2011.

(51) Int. Cl.
*A61K 31/6615* (2006.01)
*A61K 31/194* (2006.01)
(Continued)

(52) U.S. Cl.
CPC ........ *A61K 31/6615* (2013.01); *A61K 31/194* (2013.01); *A61K 31/555* (2013.01); *A61K 31/661* (2013.01); *A61K 31/664* (2013.01)

(58) Field of Classification Search
CPC .. A61K 31/194; A61K 31/555; A61K 31/661; A61K 31/6615; A61K 31/664
See application file for complete search history.

(56) References Cited

FOREIGN PATENT DOCUMENTS

DE 10 2005 018887 A1 10/2006
EP 0 304 986 A2 3/1989

OTHER PUBLICATIONS

Ghosh. The pathobiology of osteoarthritis and the rationale for the use of pentosan polysulfate for its treatment (Seminars in Arthritis and Rheumatism, vol. 28, No. 4, Feb. 1999).*

(Continued)

*Primary Examiner* — Anna Pagonakis
(74) *Attorney, Agent, or Firm* — John P. Zimmer; J. Clinton Wimbish; Smith Moore Leatherwood LLP (57) ABSTRACT

The invention is directed to a composition and associated method for the treatment of musculoskeletal related disorders and diseases. In particular, the present invention provides a class of citrate compounds that can be used to for the treatment of diseases/disorders characterized by the degeneration of musculoskeletal tissues including menisci, bone, articular cartilage, and soft tissues. Examples of suitable citrate and citrate analog compounds include citrates having the following base formula (I):

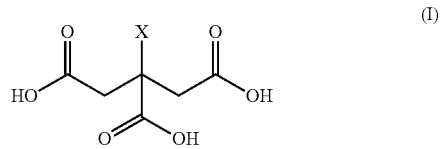

where X may be one of the following:

(Continued)

-continued

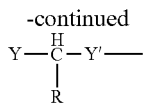

wherein Y, Y', and Y" are independently a citrate moiety, O, O—Y, OH, NH, NH—Y, R and R—Y, with R being an alkyl, alkyene, ester, aryl, or phenyl group having from 1 to 6 carbon atoms.

12 Claims, 4 Drawing Sheets

(51) Int. Cl.
  *A61K 31/555* (2006.01)
  *A61K 31/661* (2006.01)
  *A61K 31/664* (2006.01)

(56) References Cited

OTHER PUBLICATIONS

Dorwald F. Zaragoza. Side reviews in organic chemistry: a guide to successful synthesis design. Weinheim: Wiley-VCH, Verlag, GMBH & Co., KGaA, 2005. Preface.*

Cooper et al. Studes on the gastrointetinal absorption of phosphocitrate, a powerful controller of hydroxyapatite formation. International Journal of Pharmaceutics, 98, 1993, 165-172.*

DE 1020050118887. English translation attached. May 2014.*

Englund, Martin. Meniscal tear—a feature of osteoarthritis. Acta Orthopaedica Scandinavica. Supplementum No. 312, vol. 75, Apr. 2004.*

Chueng, Herman S. et al.; "Phosphocitrate Blocks Calcification-induced Articular Joint Degeneration in a Guinea Pig Model"; Arthritis & Rheumatism; vol. 54, No. 8, Aug. 1, 2006; pp. 2452-2461; XP55032837.

Sallis, J D et al.; "Phosphocitrate, a potential therapeutic agent for calcium crystal deposition diseases"; Current Rheumatology Reviews, Bentham Science; vol. 2, No. 1, Feb. 1, 2006; pp. 95-99; XP009161240.

Yubo, Sun, et al.; "Calcium deposition in osteoarthritic meniscus and meniscal cell culture"; Arthritis Research and Therapy; Biomed Central, London, GB; vol. 12, No. 2; Mar. 30, 2010; p. R56; XP021085184.

International Search Report and Written Opinion from International Application No. PCT/US2012/028705, mailed Jul. 27, 2012.

Lotz, Martin K., Posttraumatic Osteoarthritis: Pathogenesis and Pharmacological Treatment Options, Arthritis Research & Therapy 2010, 12:211, 9 pages.

Schenker, MD, Mara L. et al., Pathogenesis and Prevention of Posttraumatic Osteoarthritis After Intra-articular Fracture, J Am Acad Orthop Surg. Jan. 2014, Author manuscript, 16 pages, available in PMC May 9, 2015.

* cited by examiner

COMPOSITIONS AND METHODS FOR THE TREATMENT OF MUSCULOSKELETAL RELATED DISEASES AND DISORDERS USING METAL ION-CITRATE ANALOG COMPLEXES

CROSS REFERENCE TO RELATED APPLICATIONS

This application claims priority to and is a nonprovisional application of U.S. Provisional Application No. 61/453,401, filed Mar. 16, 2011, which is incorporated by reference herein in its entirety.

FIELD OF THE INVENTION

The present invention generally to the treatment of muscoskeletal related diseases and disorders, and in particular to the protection and regeneration of the synovium, meniscus, cartilage, and bone.

BACKGROUND OF THE INVENTION

Musculoskeletal diseases and disorders are among the most common of human afflictions. They affect all age groups and can frequently cause disability, impairments, and handicaps. They include a variety of different diseases that cause pain or discomfort in the bones, joints, muscles, or surrounding structures, and they can be acute or chronic, focal, or diffuse.

It is estimated that approximately 33 percent of U.S. adults are affected by musculoskeletal symptoms, including limitation of motion or pain in a joint. Musculoskeletal disorders range from back pain to, and include different types of arthritis, and musculoskeletal pain. Degeneration of musculoskeletal tissues is a hall mark of many musculoskeletal disease/disorders including meniscal degeneration, meniscal degenerative tear, osteoporosis, osteoarthritis, muscular dystrophy, and the like.

Current treatment options for these diseases/disorders include treatment with a pharmalogical agent, such as steroids or non-steroid, anti-inflammation drugs, or surgery. However, all current available pharmacological agents only relieve clinical symptoms and have no effect on the progression of the underlining diseases/disorders (degenerative meniscal tear, osteoarthritis, intervertebral disc degeneration, muscular degeneration, etc.) or have some undesirable side effect (for example, steroids can cause bone loss and increase the risk of infection and bisphosphonate can cause Jaw osteoporosis). For instance, non-steroid anti-inflammation drugs including Cox-2 inhibitors are often prescribed to treat joint related pain for a variety of disorders including arthritis, meniscal and ligament injuries and tears. However, the use of many of these drugs are associated with undesirable side effects including upset stomach, cramping, and bleeding. In addition, the repetitive use of steroids can be harmful to tissue and bones.

Accordingly, there still exists a need for methods of treating musculoskeletal diseases and disorders, which not only relieve clinical symptoms, but may also help inhibit the progression of the underlying disorder/disease.

BRIEF SUMMARY OF THE INVENTION

Embodiments of the present invention are directed to a composition and associated method for the treatment of musculoskeletal related disorders and diseases. In particular, the present invention provides a class of citrate analog compounds that can be used to for the treatment of diseases/disorders characterized by the degeneration of musculoskeletal tissues including menisci, bone, articular cartilage, and soft tissues. In one embodiment, not only can relieve clinical symptoms such as pain, swelling and inflammation but also can inhibit the progression of the underlying diseases or inhibit the degeneration of musculoskeletal tissues. In one embodiment, the present invention provides a method for the treatment of disorders or diseases that are associated with meniscal degeneration, meniscal tears, meniscus transplantation, and combinations thereof.

In a further aspect, embodiments of the present invention may also provide a composition and associated method for the therapeutic treatment of diseases characterized by inflammation and pathological calcification.

In one embodiment, the present invention provides a treatment for musculoskeletal related disorders and diseases in which a citrate and/or citrate analog compound (collectively referred to as a citrate analog compound) is complexed with a metal ion. The inventors of the present invention have discovered that compositions in accordance with the present invention can be used to inhibit the degeneration of musculoskeletal tissue and promote the repair and regeneration of musculoskeletal tissues, including menisci, articular cartilage, bone and soft tissues.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention are directed to compounds and compositions for the treatment of musculoskeletal related diseases and disorders. In particular, the present invention is directed to the treatment of musculoskeletal diseases associated with the degeneration of musculoskeletal tissues. For example, the present invention can be used to treat degeneration of musculoskeletal tissues including diseases or disorders associated with meniscal degeneration, meniscal degenerative tear, bone loss and cartilaginous degeneration. In one particular embodiment, the present invention provides a method for the treatment of disorders or diseases that are associated with meniscal degeneration, meniscal tears, meniscus transplantation, and combinations thereof.

In one embodiment, compounds and compositions in accordance with the present invention are directed to citrate and citrate analog compounds and pharmaceutically acceptable salts thereof. In a further aspect, embodiments of the present invention is directed to compounds and compositions comprising citrate and citrate analog compounds and pharmaceutically acceptable salts thereof that are complexed with one or more metal ions.

Examples of suitable citrate and citrate analog compounds include citrates having the following base formula (I):

(I)

where X may be one of the following:

wherein Y, Y', and Y" are independently a citrate moiety, O, O—Y, OH, NH, NH—Y, R and R—Y, with R being an alkyl, alkyene, ester, aryl, or phenyl group having from 1 to 6 carbon atoms; and Z is a carboxyl group, H, or R.

In formula (I) above, the citrate compound is depicted in the form of an acid. It should be recognized that pharmaceutically acceptable salts of formula (I) are also embraced within the compounds of the present invention. The term "pharmaceutically acceptable salt" denotes, in the context of this invention, salts of at least one of the compounds according to the invention—usually a (deprotonated) acid—as an anion with at least one, preferably inorganic, cation, which are pharmaceutically and physiologically acceptable, in particular when administered to humans and/or mammals. The salts of the alkali and alkaline-earth metals are particularly preferred, but also $NH^{4+}$, in particular however (mono), (di) sodium or (tri) sodium, (mono) or (di) potassium, magnesium or calcium salts.

In a further embodiment, suitable citrate and citrate analog compounds include citrates having the following base formula (II):

(II)

wherein X is the same as described above with respect to formula (I).

The following compound are representative examples of citrate and citrate analog compounds that may be used embodiments of the present invention:

-continued

In a further aspect of the invention, the inventive citrate and citrate analog compounds and pharmaceutically acceptable salts thereof may be complexed with one or more metal ions. The inventors of the present invention have surprisingly and advantageously discovered that complexing a citrate or citrate analog with a metal ion, the biological activities of the citrate and citrate analog compounds was enhanced. In particular, the inventors have discovered that the invention metal ion citrate complexes surprisingly stimulate bone formation.

Suitable metal ions include divalent and trivalent metal ions, such as magnesium (Mg), manganese (Mn), calcium (Ca), strontium (Sr), iron (Fe), zinc (Zn), aluminum (Al) and combinations thereof. The ratio of metal ion to the citrate and citrate analog compounds is typically from about 1:6 to 3:1, with a ratio of 1:1 being preferred.

In one embodiment, the citrate and citrate analog compounds, and the metal ion citrate analog complexes can be combined with a polysaccharide, such as chondroitin sulfate or hyaluronic acid. When present, the ratio of the citrate analog/metal ion citrate analog complex to the polysaccharide is from about 1:4 to 3:1, and in particular from about 1:2 to 2:1. It has generally been found for primary diseases, such as osteoarthritis, a relatively high ratio may be preferred, and in the case of trauma-induced acute conditions, such as posttraumatic osteoarthritis, a relatively low ratio is preferred.

In a further aspect of the present invention, the citrate and citrate analog compounds, and the metal ion citrate analog complexes can be combined with a steroid, such as glucocorticoids. When present, the ratio of the citrate analog/metal ion citrate analog complex to the polysaccharide is from about 1:1 to 1:4, and in particular from about 1:2 to 2:1.

The compounds and compositions of the present invention may be administered by any suitable means, including direct administration (e.g., locally by injection or topical administration at a treatment site) or systemically (e.g., parenterally or orally), or implantation.

The pharmaceutical compositions and compounds as utilized in this invention can be administered by intranasal, oral, inhalational, enteral, topical, rectal, intramuscular, intrapleural, intraventricular, intraperitoneal, ophthalmic, intravenous, implantation or subcutaneous means.

If desired, a given compound or composition may be adapted to different situations by association with a suitable molecule, materials and/or cells (meniscal cells, chondrocyte or stem cells). For example, the citrate analog complexes and metal ion citrate analog complexes may be made more soluble or dispersible in physiological solutions than the corresponding original form, or it can be mixed with carriers and cells, and implanted in proper site such as bone defects.

The compositions containing the compound of the present invention may be supplied in liquid or solid form. Compositions in accordance with the present invention may further include solvents, diluents, excipients, preservatives, emulsifiers, polymers, compounds for adjusting odor, taste, pH or the like.

The formulations can be administered with or without additional carrier or diluent by the oral, systemic injections, percutaneous, transmucosal, or other typical route. Pharmaceutical formulations in accordance with the present invention may be administered orally in caplet, tablet, particle, granule, or powder forms. The present invention provides a method of treating and/or ameliorating the effects of musculoskeletal related diseases and disorders by administering a therapeutically effective amount and/or a prophylactic amount of the aforementioned citrate and citrate analog compounds or a pharmaceutically acceptable salt thereof, to a sufferer in need thereof. According to the present invention, a "therapeutically effective amount" of a compound, combination or pharmaceutical composition of the invention is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect. Typical dosage amounts may range from about 0.1 to 60 mg/kg body weight, and in particular from about 1 to 20 mg/kg body weight. In one embodiment, the dosage amount is from about 10 to 20 mg/kg body weight.

The dosage administered will, of course, vary depending on the use and known factors such as the pharmacodynamic characteristics of the active ingredient; age, health, and weight of the recipient; nature and extent of symptoms; kind of concurrent treatment, frequency of treatment, and the effect desired. The recipient may be any type of mammal, but is preferably a human. In one embodiment, dosage forms (compositions) of the inventive composition may contain about 0.1 microgram to 1,000 micrograms of active ingredient per unit, and in particular, from about 10 to 100 micrograms of active ingredient per unit.

For use in the treatment of targeted musculoskeletal related diseases and disorders, by way of general guidance, a daily oral dosage of the active ingredient (i.e., citrate, citrate analog, or metal ion citrate analog complex) can generally range from about 0.2 to 20 mg/kg of body weight. It should be recognized that the dosage can be raised or lowered based on individual patient response. It will be appreciated that the actual amounts of active compounds used will vary according to the specific compound being utilized, the particular compositions formulated, the mode of application, and the particular site of administration.

The citrate and citrate analog formulations of the present invention may also be coupled with inorganic salts including calcium phosphate and calcium sulfate.

The compositions described herein may be administered as part of a sustained-release formulation (i.e., a formulation such as a capsule or resin or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane. Carriers for use within such formulations are bio-compatible, and may also be biodegradable; preferably the formulation provides a relatively constant level of modulating agent release. The amount of modulating agent contained within a sustained-release formulation depends upon the site of implantation, the rate and expected duration of release and the nature of the condition to be treated or prevented.

In one embodiment, the pharmaceutical compositions and compounds of the present invention are administered topically, especially when the target of treatment includes areas or organs readily accessible by topical application, including diseases of the eye, or the skin. Topical application may also be readily used to administer the combinations, compounds and compositions of the invention to tissue below the skin, such as muscle. Suitable topical formulations may be prepared for each of these areas or organs.

Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

When formulated in an ointment, the active ingredients may be employed with either paraffinic or a water-miscible ointment base. Alternatively, the active ingredients may be formulated in a cream with an emulsified cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include methocarbamol, longer-chain alcohols, dimethylsulfoxide and related analogs.

Also included within the invention are preparations for topical application to the skin comprising a compound of the invention, typically in concentrations in the range from about 0.1% to 2%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, flavouring agents, colouring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, flavoring agents, coloring agents, and the like.

The following Examples are provided to illustrate embodiments of the invention and are not intended to limit the invention in any way.

EXAMPLES

Example 1

One month old C57/BL6 mice were divided into two groups. The first group of mice received 60 mg/kg sodium phosphocitrate (NaPC) via intraperitoneal injection twice per week and the second group of mice received intraperitoneal injections of saline as controls. Two months later, the animals were sacrificed and examined with high definition X-ray. Representative X-ray images are shown in FIG. 1. As shown, NaPC treatment promoted the formation of bone. In images A and B of FIG. 1, it can be seen that the diameters of the front limbs of PC-treated mice (red arrows) were larger than the diameters of the front limbs of untreated mice (blue arrows). In images C and D of FIG. 1, it can be seen that the bone mineral contents in the hind limbs of PC-treated mice (red arrows) were higher than the bone mineral contents of the hind limbs of untreated mice (blue arrows). Accordingly, it can be seen that the citrate complexes in accordance with the present invention can be used for the treatment of musculoskeletal related diseases, and in particular, for the promotion of bone growth.

Example 2

Figure 1A:
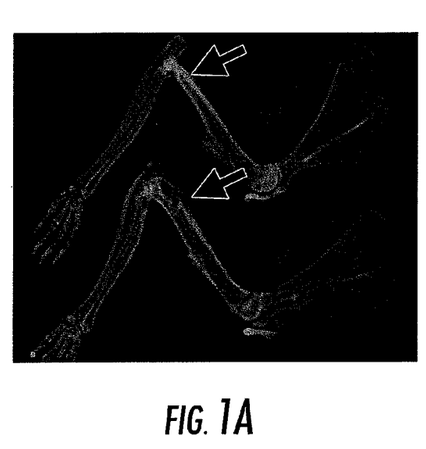
FIG. 1 are high definition X-ray images of the limbs of one month old C57/BL6 mice that were treated with a composition in accordance with the present invention in comparison to a control group.
Figure 1B:
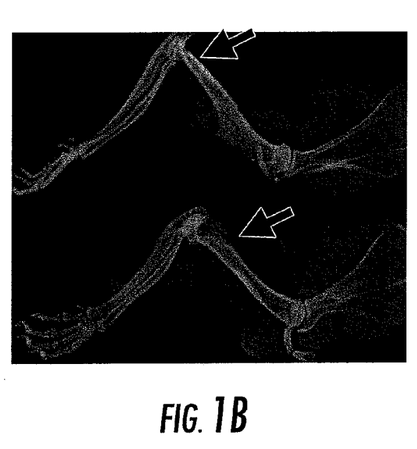
Figure 1C:
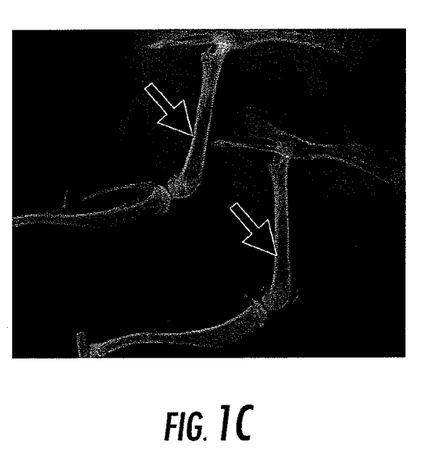
Figure 1D:
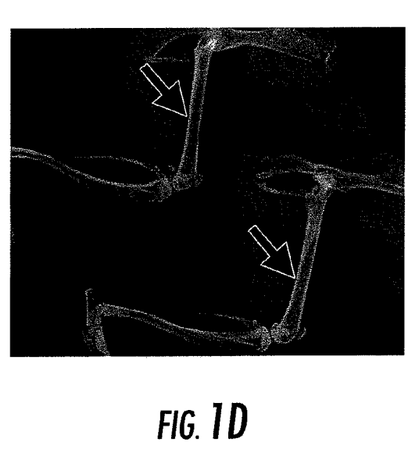
Figure 2A:
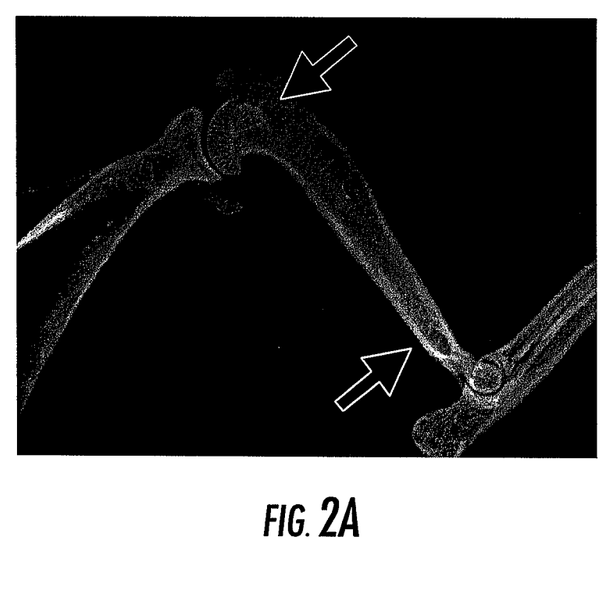
FIG. 2 are high definition X-ray images of the limbs of Hartley guinea pigs that were treated with a composition in accordance with the present invention in comparison to a control group.
Figure 2B:
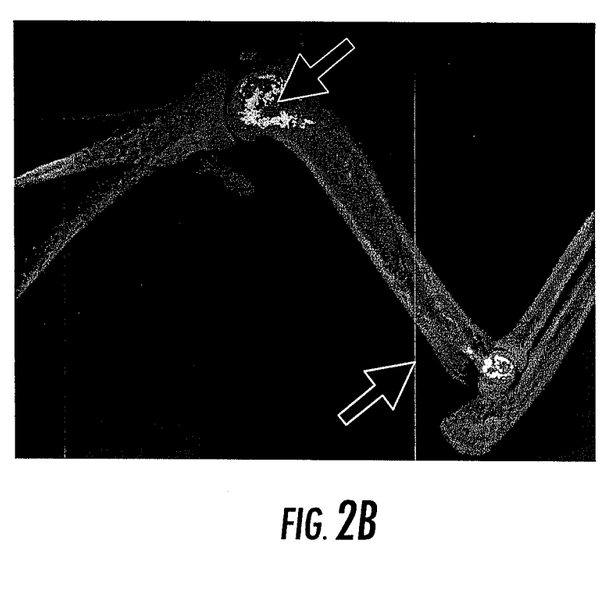

In this example, three month old Hartley guinea pigs were administered 30 mg/kg calcium phosphorcitrate (CaPC) or saline via intraperitoneal injection twice per week. Eight months later, the guinea pigs were sacrificed and examined with high definition X-ray. Representative X-ray images are shown in FIG. 2. The X-ray images of the front limbs of Hartley guinea pigs show that the diameter of the front limb of a CaPC-treated Hartley guinea pig (right photo, the red arrow) was larger than the diameter of the front limb of an untreated Hartley guinea pig (left photo, the red arrow). The bone mineral content of the front limb of a CaPC-treated Hartley guinea pig (left photo, the green arrow) was higher than the bone mineral content of a front limb of an untreated Hartley guinea pig (left photo, the green arrow). As shown in FIG. 2, CaPC treatment promoted the formation of bone in Hartley guinea pigs. The diameter of the front limb was lager and the bone mineral content was higher in CaPC-treated Hartley guinea pigs that that in untreated Hartley guinea pigs.

Figure 3:
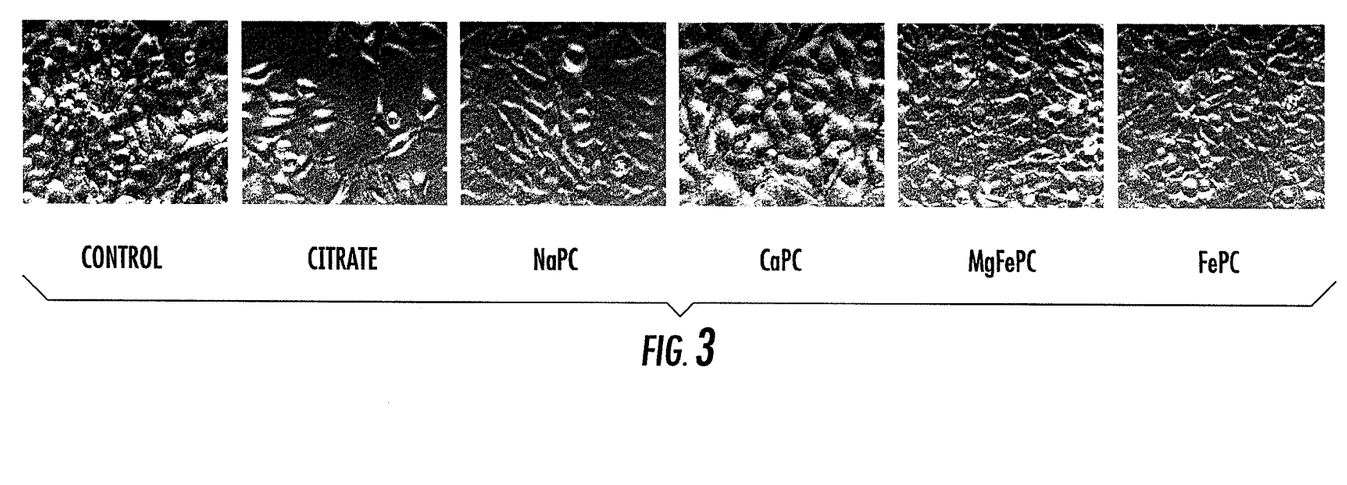
FIG. 3 are Micro-CT scan images of the femurs of Hartley guinea pigs of FIG. 2.

The distal femurs of the Hartley guinea pigs were also analyzed with Skyscan Micro-CT. Representative images are shown in FIG. 3. The femur of untreated Hartley guinea pigs had less bone volume and larger marrow space than the femur of CaPC-treated Hartley guinea pigs. Micro-CT scan of the femur of Hartley guinea pigs. In particular, the left Micro-CT image of FIG. 3 shows the femur of an untreated Hartley guinea pig. The area showing less trabecular bone and larger marrow space is indicated by a red arrow. In the right image of FIG. 3, the femur of a CaPC-treated Hartley guinea pig is shown. The area showing more trabecular bone and less marrow space is indicated by a red arrow. Quantitative data is provided in table 1 below.

TABLE 1

Bone measurements obtained from Micro-CT.

| | Bone Volume | Tissue Volume | Trabecular Thickness | Trabecular Number |
|---|---|---|---|---|
| Untreated guinea pigs | 0.19 ± 0.04 | 10.76 ± 1.9 | 32.90 ± 3.6 | 0.43 ± 0.08 |
| Treated guinea pigs | 0.49 ± 0.09 | 10.76 ± 1.9 | 42.00 ± 4.9 | 1.07 ± 0.15 |

Femurs, previously stored in 70% ethanol, were cut close to the distal femur condyle. The specimens were left to dry 48-hr before being scanned using Skyscan Micro-CT. A 3-D model was built in the ANT model building program and bisected with a plane down the lateral/midline. Using the model building program, a separate dataset was built forming 30 cross sections on either side of the plane. With this dataset, measurements were taken with the 3D-Calc program. A rectangular region of interest was applied to all 60 sections. The region of interest was placed approximately 0.5 cm down from the growth plate in the central part of the trabeculae and extended downward.

The bone mineral density of subchondral bone of these same Hartley guinea pigs was evaluated using a X-ray densitometry. The results are shown in Table 2 below.

TABLE 2

Subchondral bone mineral density from X-ray densitometry.

| | Pair one $g/cm^2$ | Pair two $g/cm^2$ | Pair three $g/cm^2$ |
|---|---|---|---|
| Untreated guinea pigs | 0.143 | 0.146 | 0.150 |
| CaPC-treated guinea pigs | 0.157 | 0.161 | 0.181 |

The micro-CT data (Table 1) has confirmed the observation with the use of high definition X-ray (FIG. 2). It demonstrated that metal ion-citrate analog treatment strongly stimulated the formation of bone tissues compared to the untreated Hartley guinea pigs. Metal ion-citrate analog complex treatment not only increased the thickness of the trabecular but also the trabecular numbers. Bone mineral density examination (Table 2) demonstrated that metal ion-citrate analog treatment promoted mineral deposition in the subchondral bone, which supports its application in osteoarthritis and osteoporosis.

Example 3

In this example, meniscus derived from osteoarthritis patients were minced into small pieces and cultured in the absence or presence of magnesium phosphcitrate (MgPC). After 7 day treatment, RNA was extracted and gene expression was investigated using microarray. The results indicated that MgPC inhibited the expression of numerous genes involved in the degeneration of extracellular matrix, pain response and inflammation, and concurrently stimulated the expression of numerous genes involved in the regeneration of musculoskeletal tissues. The results are shown in Table 3, below.

TABLE 3

Gene Expression resulting from magnesium phosphcitrate (MgPC) treatment

| Biological process | Gene Name | Differential Expression | Description |
|---|---|---|---|
| Inflammatory Response | IL1b | −2.0 | Interleukin 1, beta |
| | IL6 | −2.0 | Interleukin 6 (interferon, beta 2) |
| | IL8 | −2.2 | Interleukin 8 |
| Proteolysis | MMP9 | −2.7 | Matrix metallopeptidase 9 |
| | ADAMTS5 | −2.1 | ADAM metallopeptidase with thrombospondin type 1 motif 5 |
| | ADAMDEC1 | −7.1 | ADAM-like, decysin 1 |
| Skeletal Development | ACAN | 2.0 | Aggrecan |
| | COL2A1 | 2.0 | Collagen, type II, alpha 1 |
| | COL11A1 | 2.7 | Collagen, type XI, alpha 1 |

As can be seen from Table 3, MgPC down-regulated the expression of inflammatory cytokines IL-1β, IL-6 and IL-8, which have been previously implicated in arthritis. MgPC also down-regulated the expression of matrix metalloproteinase-9 (MMP9), ADAM metallopeptidase with thrombospondin type 1 motif 5 (ADAMTS5) and ADAM-like, decysin 1 (ADAMDEC1). Significantly, many of the genes encoding the key extracellular matrix proteins of meniscus including collagen, type II, alpha 1 (COL2A1), collagen, type XI, alpha 1 (COL11A1) and aggrecan (ACAN) were significantly induced by CaPC treatment. This experiment has been repeated three times.

Example 4

Figure 4:
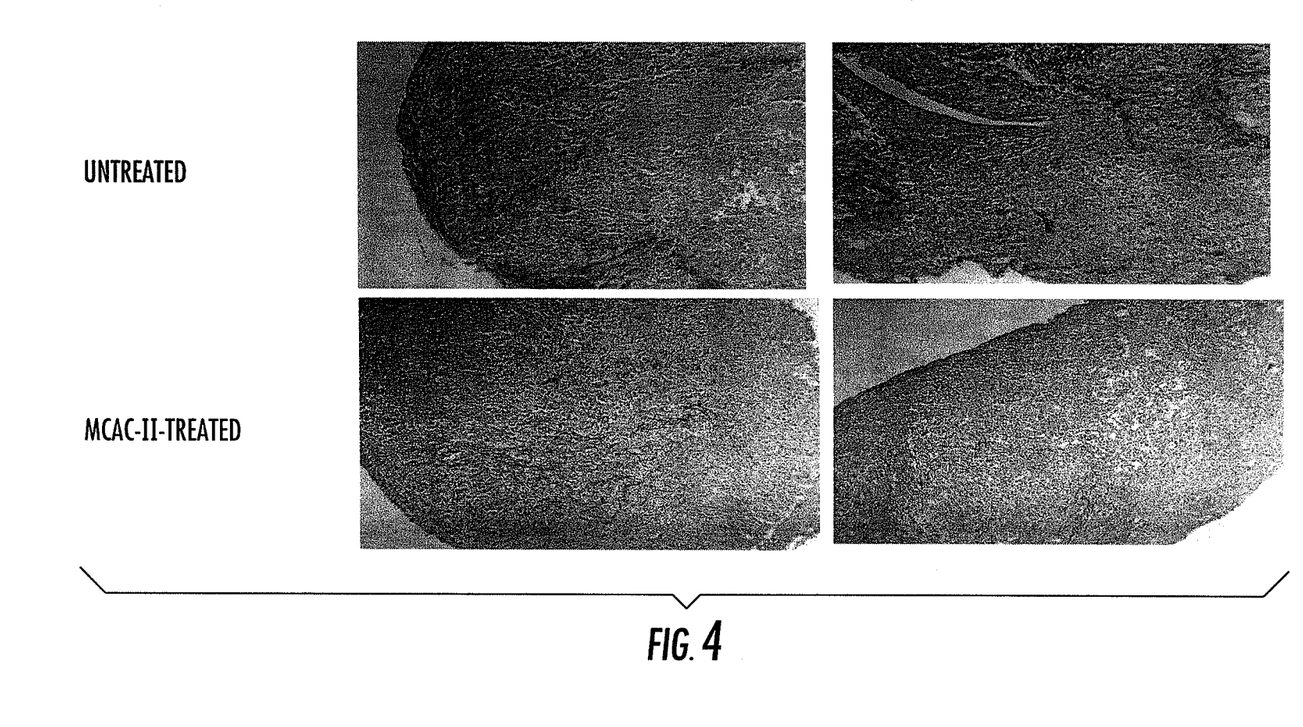
FIG. 4 are images of picrosirius red staining of micromasses of meniscal cells that were treated with a composition in accordance with the present invention in comparison to a control group.

In this example, micromasses of meniscal cells were cultured at the absence or presence of a citrate analogue compound for 14 days. The production of collagens was then examined with picrosirius red staining. As shown in FIG. 4, there was much stronger picrosirius red staining in the citrate analogue compound-treated micromasses of meniscal cells than that in the untreated micromasses. This result indicated that the citrate analog compound stimulated the production of collagens by meniscal cells, which was consistent with the gene expression data presented in the Table 3. Taken together, the experimental results demonstrate that citrate analog compounds in accordance with the present invention are meniscus-protective and meniscus-regenerative agents, and can be used for the treatment of meniscal tear, meniscal degeneration or for meniscus regeneration.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating a musculoskeletal disease or disorder comprising the step of administering to a subject in need thereof an effective amount of a composition comprising a citrate compound or a pharmaceutically acceptable salt thereof that is complexed with a metal ion, wherein the musculoskeletal disease or disorder is posttraumatic osteoarthritis, and wherein the citrate compound has the following formula:

where X is one of the following:

wherein Y is a citrate moiety, O, OH, NH, or R; Y' and Y" are independently a citrate moiety, O, O—Y, OH, NH, NH—Y, R or R—Y, with R being an alkyl, alkene, ester, or aryl group having from 1 to 6 carbon atoms; and Z is a carboxyl group, H, or R.

2. The method of claim 1, wherein the ratio of metal ion to citrate compound is from about 1:6 to 2:1.

3. The method of claim 1, wherein the composition is administered at a dosage from about 2 mg to 200 mg/kg body weight.

4. The method of claim 1, wherein the composition is administered orally.

5. The method of claim 1, further comprising administering chondroitin sulfate, pentosan polysulfate, or a combination thereof.

6. The method of claim 1, wherein the disorder or disease is further characterized as osteoporosis or invertebral disc degeneration.

7. The method of claim 1, wherein the disorder or disease is associated with meniscal degeneration, meniscal tears, meniscus transplantation, and combinations thereof.

8. The method of claim 1, wherein the metal ion is selected from the group consisting of magnesium (Mg), calcium (Ca), strontium (Sr), iron (Fe), zinc (Zn) and combinations thereof.

9. The method of claim 1, wherein the citrate comprises phosphocitrate and the metal ion is selected from the group consisting of sodium, magnesium, iron, and calcium.

10. The method of claim 1, wherein X is and Y" is O; Y' and Y are OH.

11. A method for treating a musculoskeletal disease or disorder comprising the step of administering to a subject in need thereof an effective amount of a composition comprising a citrate compound or a pharmaceutically acceptable salt thereof that is complexed with a metal ion, wherein the citrate compound comprises a compound having the following base formula (I):

where X is one of the following:

wherein Y is a citrate moiety, O, OH, NH, or R; Y' and Y" are independently a citrate moiety, O, O-Y, OH, NH, NH-Y, R or R-Y, with R being an alkyl, alkene, ester, or aryl group having from 1 to 6 carbon atoms, and wherein the musculoskeletal disease or disorder is posttraumatic osteoarthritis.

12. The method of claim 11, wherein the metal ion is selected from the group consisting of magnesium (Mg), manganese (Mn), calcium (Ca), strontium (Sr), iron (Fe), zinc (Zn), aluminum (Al) and combinations thereof, and the ratio of metal ion to citrate compound is from about 1:6 to 2:1.

* * * * *